United States Patent [19]

Shimatani et al.

[11] Patent Number: 5,041,080
[45] Date of Patent: Aug. 20, 1991

[54] TAMPON APPLICATOR

[76] Inventors: Sumie Shimatani; Kazuo Shimatani, both of 109-3 Kovato, Kouza-gun, Samukawa-machi, Kanagawa, Japan

[21] Appl. No.: 598,634
[22] PCT Filed: Apr. 11, 1989
[86] PCT No.: PCT/JP89/00384
 § 371 Date: Dec. 12, 1990
 § 102(e) Date: Dec. 12, 1990
[87] PCT Pub. No.: WO89/09585
 PCT Pub. Date: Oct. 19, 1989

[30] Foreign Application Priority Data
 Apr. 12, 1988 [JP] Japan .................................. 63-48866

[51] Int. Cl.⁵ .............................................. A61F 13/26
[52] U.S. Cl. ......................................... 604/13; 604/11; 604/15
[58] Field of Search ...................... 604/11, 12, 13, 14, 604/15, 16, 17, 18

[56] References Cited
U.S. PATENT DOCUMENTS

| 545,102 | 8/1895 | Sleem | 604/15 |
| 4,048,998 | 9/1977 | Nigro | 604/14 |
| 4,198,978 | 4/1980 | Nigro | 604/15 |
| 4,276,881 | 7/1981 | Lilaonitkul | 604/14 |
| 4,543,086 | 9/1985 | Johnson | 604/15 |

FOREIGN PATENT DOCUMENTS
 2204491 11/1988 United Kingdom ................... 604/11

Primary Examiner—Paul J. Hirsch
Attorney, Agent, or Firm—Edwin E. Greigg; Ronald E. Greigg

[57] ABSTRACT

Disclosed herein is a tampon applicator having a tampon for physiological use to absorb woman's menstrual blood, and comprising a rotatable member connected to a trailing end of the applicator and rotated to thereby cause the tampon to be protruded from and retracted into an outer cylindrical member of a case. The tampon in its spared state is thus held within the outer cylindrical member so that the applicator can be made small-sized and easy to carry. The tampon applicator is easily used by simply rotating only the rotatable member, without fear of staining fingers wherein protrusion of the tampon out of the case can be adjusted by rotation of the rotatable member so that a user can protrude the tampon to a desired length most appropriate to her before she inserts the tampon in her vagina, whereby she can use the applicator with a reduced feeling of disorder or incongruity because the tampon is inserted together with the case after protruded therefrom.

1 Claim, 2 Drawing Sheets

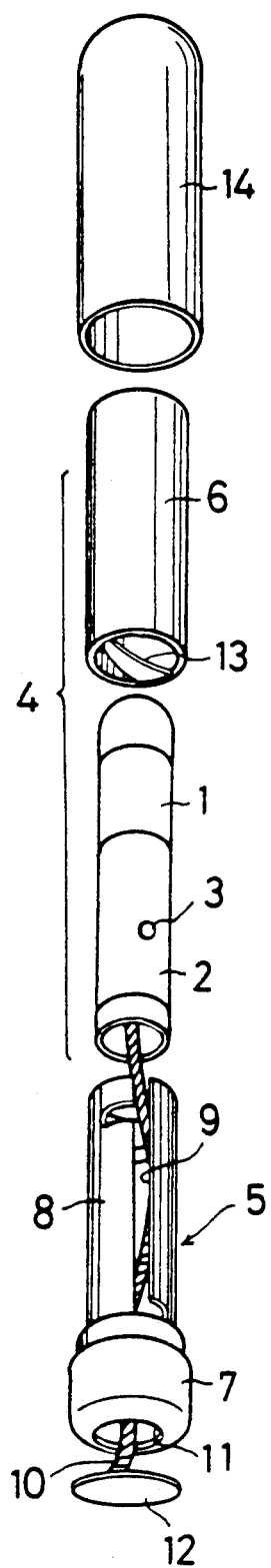
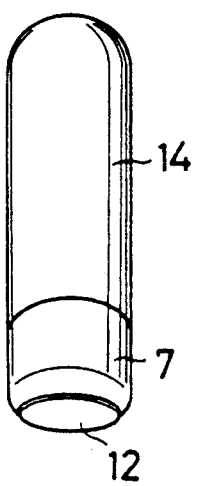
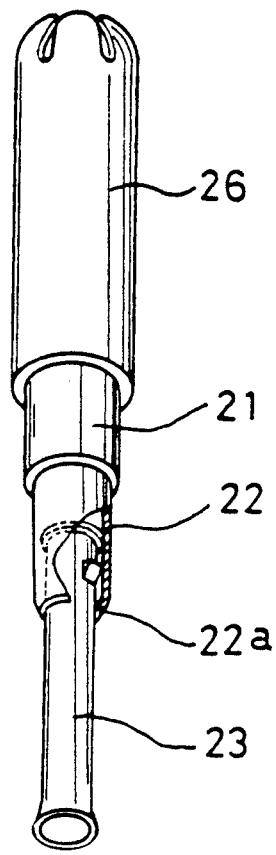
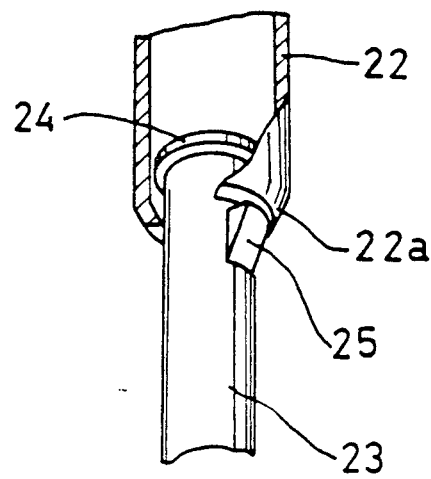

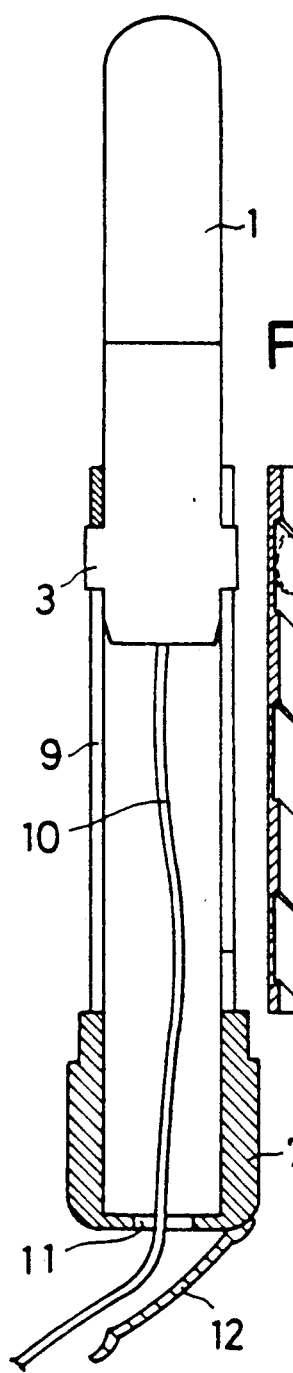
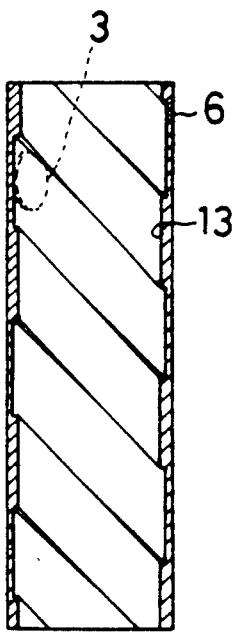
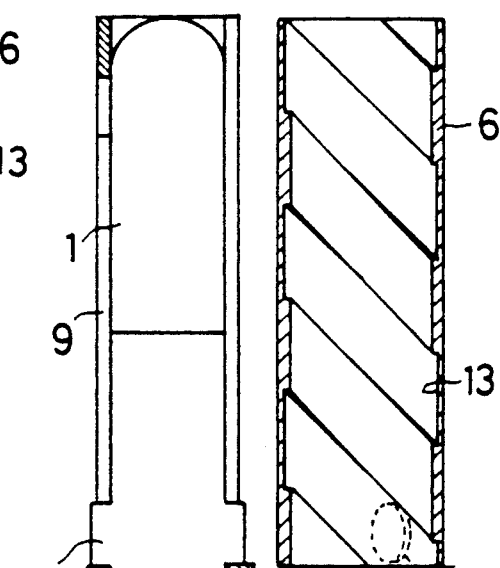
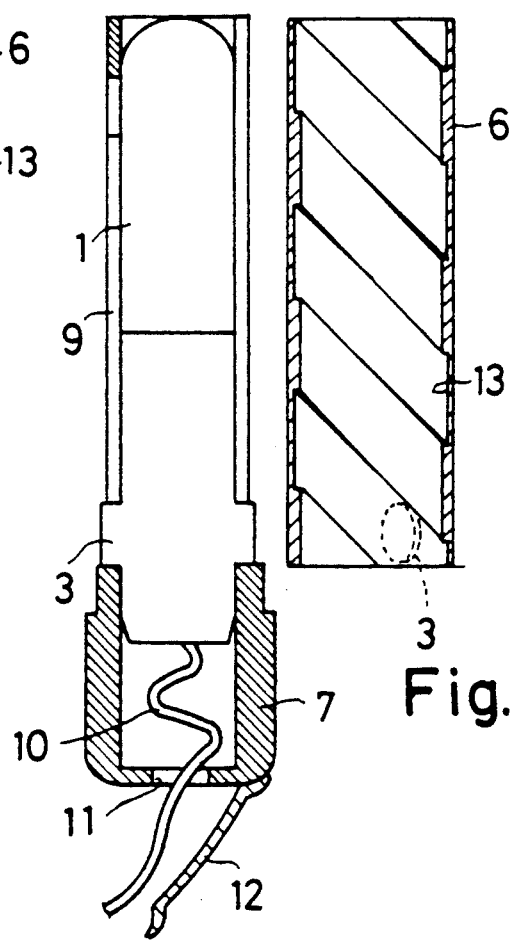

TAMPON APPLICATOR

FIELD OF THE INVENTION

The invention relates to a tampon applicator which is not bulky to carry, is easy to use and its depth of insertion can be readily adjusted.

PRIOR ART

There is known a tampon applicator which comprises an outer cylindrical member having at its end a compressed tampon of a bullet-like shape, and an inner cylindrical member inserted in the outer cylindrical member and adapted to push the tampon outwards.

It is however to be noted that in such a known structure an overall length of the applicator corresponds to a total of lengths of the outer and inner cylindrical members, and thus makes it not convenient to carry.

Therefore, a new type of tampon applicator has been proposed recently as shown in FIG. 5 wherein a protection cap 26 protects the applicator which comprises the outer cylindrical member 21, the inner cylindrical member 22 and a push rod 23. In this applicator, the inner cylindrical member 22 is inserted in the outer cylindrical member 21, and the push rod 23 is inserted in the inner cylindrical member 22, in such a state that before use of said applicator the overall length thereof is nearly equal to the length of the outer cylindrical member 21. When it is used, the inner cylindrical member 22 and the push rod 23 are pulled out so as to increase the length of the applicator into a total length of those three members. Owing to this feature, the newly proposed tampon applicators have been taking place of the older known ones.

In such a 'three-staged' structure as employed in the newer applicators, the push rod 23 must be pulled at first to forcibly fit a trailing end 22a of the inner cylindrical member 22 in a gap between an annular protrusion 24 formed at extremity of said rod and a lug 25. This operation which is done to tightly connect the push rod 23 to the inner cylindrical member 22 is however not easy. Further, this operation is carried out after the outer cylindrical member has been inserted into a user's vagina, whereby her fingers are likely to be stained with menstrual blood.

The invention was made in view of those problems in order to provide a tampon applicator which is compact before use, and is easy to be adjusted into a desired length when it is used, and further is not apt to stain user's fingers when it is used.

DISCLOSURE OF THE INVENTION

The invention provides a tampon applicator which comprises a tampon compressed into a bullet-like shape, a supporting member supporting a trailing end of the tampon, a case housing the tampon and the supporting member, a rotatable member attached to a trailing end of the case, a motion converting mechanism causing the tampon to linearly go out of and come back into a leading end portion of the case when the rotatable member is rotated, and a string connected to the tampon and capable of being pulled outwards through a bottom of the rotatable member.

The tampon applicator has at a trailing end thereof the rotatable member which can be rotated to move the tampon forwards and backwards within an outer cylindrical member of the case. The tampon in its spared state is thus held within the outer cylindrical member so that the applicator which is provided by the invention can be small-sized and easy to carry.

Contrary to the known applicators, any operating rod and inner cylindrical member need no more be pulled out of a trailing end of the outer cylindrical member, and these cylindrical members also need not be connected to each other when the applicator in the invention is used. The tampon applicator in the invention is thus easily used by simply rotating only the rotatable member, without fear of staining fingers.

In particular, protrusion of the tampon out of the case can be adjusted by rotation of the rotatable member so that a user can protrude it to a length most appropriate to her before she inserts the tampon in her vagina. This reduces a feeling of disorder or incongruity which has been unavoidable in the known applicators wherein the tampon is protruded after insertion of the case into vagina.

BRIEF DESCRIPTION OF THE DRAWINGS

FIG. 1 is a perspective view showing a disassembled state of a tampon applicator in an embodiment of the invention; FIG. 2 is a perspective view showing the tampon applicator in its packed state; FIGS. 3a, 3b, 4a and 4b are cross sections respectively showing in disassembled state the operation of the tampon applicator; FIG. 5a is a perspective view showing a known applicator with its portion cut off; and FIG. 5b is an enlargement of its important part.

PREFERRED EMBODIMENTS OF THE INVENTION

Embodiments of the invention will now be described in detail referring to the drawings.

In FIGS. 1 to 4 showing a tampon applicator in an embodiment of the invention, the reference numeral 1 denotes a tampon which is compressed into a bullet-like shape, and the numeral 2 denotes a supporting member which, in order to support a trailing end of the tampon, engages with a lower portion of the tampon to such a degree that the tampon may not fall off an upper end of a case described below. The reference numeral 3 denotes a lug formed on a peripheral surface of the supporting member.

The case 4 mentioned above comprises an inner cylindrical member 5 and an outer cylindrical member 6. The inner cylindrical member 5 comprises a knob 7 formed at a bottom of said member and of a diameter larger than that of a cylindrical portion 8. The cylindrical portion 8 is formed integral with and upright from the knob 7. An upper end of the cylindrical portion 8 is open, and two vertical slots 9 are formed along and through a peripheral wall of the portion 8. The vertical slots 9 are of a width which allows the lug 3 of the supporting member 2 to be inserted. An upper end and a lower end of each slot 9 respectively turn to horizontal slots extending in opposite directions. A bottom of the abovementioned knob 7 has an opening 11 through which inserted is a string 10 used to pull off the tampon 1. The opening 11 is temporarily closed with a covering sheet 12 which can be peeled.

The outer cylindrical member 6 has such an inner diameter as enabling the insertion of the inner cylindrical member 5 in which the tampon 1 and the supporting member 2 are disposed. A helical groove 13 is formed on an inner peripheral surface of the outer cylindrical member, as shown in FIGS. 3 and 4. The helical groove 13 receives the lug 3 outwardly penetrating through the vertical slots 9, and guides said lug so as to cause the tampon 1 and the supporting member 2 to rotate and move fore and aft within the outer cylindrical member 6.

The numeral 14 denotes a protection cap which is of an inner diameter allowing the outer cylindrical member 6 to be inserted, and is of an outer diameter substantially equal to that of the knob 7 ( see FIG. 2 ).

It is desirable that the abovementioned parts except for the tampon 1 are made of a plastics which can be dissolved in water in a retarded manner.

In operation, a user must at first peel the covering sheet 12 of the knob 7 to thereby enable access to the string 10. Subsequently, she removes the protection cap 14 and rotates the knob 7 whereby the lug 3 is guided along the helical groove 13 on the internal surface of the outer cylindrical member so that the lug moves upwardly along the vertical slots 9. The tampon 1 thus protrude upwardly a distance or length from the upper end of the outer cylindrical member 6, the distance corresponding to an angle of rotation of said knob. She can in this way adjust the protruded distance of tampon 1 to a desired length appropriate to her, the thus protruded portion of the tampon being then inserted into her vagina. The inserted tampon 1, which is weakly connected at its trailing end to the supporting member 2 not to spontaneously fall off, will be easily separated therefrom if it is pressed by vagina while the outer cylindrical member 6 is pulled.

The case and other parts remaining in her hand may be discarded into a toilet stool, and nevertheless it will not become clogged therewith because they are made of the watersoluble material.

The tampon applicator causes no inconvenience when carried by users, because it maintains its shape of a short cylinder until prolonged to a desired length in use. Besides, it is easy to handle because it can be prolonged to the desired length merely by rotating the knob.

In the embodiment described above, the knob as a "rotatable member" is rotated in order to turn the tampon to protrude from and be retracted into the case, by means of a mechanism comprising the helical groove, the vertical slots and the lug sliding along and within these groove and slots. However, the invention may be embodied with any other known "motion converting mechanism" which is structured such that rotation is converted into linear motion whereby the tampon itself is not rotated but linearly moved fore and aft.

What is claimed is:

1. A tampon applicator which comprises a tampon compressed into a bullet-like shape, a supporting member supporting a trailing end of the tampon, a case housing the tampon and the supporting member, a rotatable member attached to a trailing end of the case, a motion converting mechanism causing the tampon to linearly go out of and come back into a leading end portion of the case when the rotatable member is rotated, and a string connected to the tampon and capable of being pulled outwards through a bottom of the rotatable member.

* * * * *